US011710229B2

(12) United States Patent
Liu et al.

(10) Patent No.: US 11,710,229 B2
(45) Date of Patent: Jul. 25, 2023

(54) METHODS AND SYSTEMS FOR SHEAR WAVE ELASTOGRAPHY

(71) Applicant: GE Precision Healthcare LLC, Milwaukee, WI (US)

(72) Inventors: Gang Liu, Wuxi (CN); Rong Lu, Wuxi (CN); Yincheng Lu, Suzhou (CN); Feng Wu, Wuxi (CN); Wei Jiang, Jiangsu (CN)

(73) Assignee: GE Precision Healthcare LLC, Milwaukee, WI (US)

( * ) Notice: Subject to any disclaimer, the term of this patent is extended or adjusted under 35 U.S.C. 154(b) by 120 days.

(21) Appl. No.: 16/826,786

(22) Filed: Mar. 23, 2020

(65) Prior Publication Data
US 2021/0295500 A1    Sep. 23, 2021

(51) Int. Cl.
*G06T 7/00* (2017.01)
*A61B 8/08* (2006.01)
*A61B 8/00* (2006.01)

(52) U.S. Cl.
CPC ............ *G06T 7/0012* (2013.01); *A61B 8/085* (2013.01); *A61B 8/463* (2013.01); *A61B 8/485* (2013.01); *G06T 2207/10136* (2013.01); *G06T 2207/20081* (2013.01); *G06T 2207/20084* (2013.01); *G06T 2207/30096* (2013.01)

(58) Field of Classification Search
CPC ......... G06T 7/0012; G06T 2207/10136; G06T 2207/20081; G06T 2207/20084; G06T 2207/30096; G06T 2207/10132; G06T 19/20; G06T 7/174; G06T 2207/20104; A61B 8/085; A61B 8/463; A61B 8/485
See application file for complete search history.

(56) References Cited

U.S. PATENT DOCUMENTS

| | | | |
|---|---|---|---|
| 2013/0310690 A1 | 11/2013 | Chang et al. | |
| 2015/0148674 A1* | 5/2015 | Park | A61B 8/485 600/438 |
| 2016/0166236 A1 | 6/2016 | Hyun | |
| 2017/0231599 A1 | 8/2017 | Jago | |
| 2018/0055479 A1* | 3/2018 | Lalena | A61B 8/4461 |
| 2018/0211392 A1 | 7/2018 | Kim | |
| 2020/0037993 A1 | 2/2020 | Makkiabadi | |

(Continued)

OTHER PUBLICATIONS

International Application No. PCT/US2021/022540 filed Mar. 16, 2021—International Search Report and Written Opinion dated Jul. 12, 2021; 10 pages.

*Primary Examiner* — Vu Le
*Assistant Examiner* — Winta Gebreslassie
(74) *Attorney, Agent, or Firm* — McCoy Russell LLP

(57) ABSTRACT

Various methods and systems are provided for ultrasound imaging. In one embodiment, a method comprises acquiring, with an ultrasound transducer of a scanning apparatus during an ultrasound scan of a patient, an ultrasound image, detecting, with an artificial intelligence model, a region of interest within the ultrasound image including a possible tumor, acquiring, with the ultrasound transducer, an elastic image of tissue within the region of interest, and displaying, with a display device, the elastic image. In this way, shear wave elastography may be automatically targeted to a region of interest, thereby reducing the processing load for the analysis and enabling a higher elasticity imaging frame rate for three-dimensional ultrasound imaging.

20 Claims, 7 Drawing Sheets

(56) References Cited

U.S. PATENT DOCUMENTS

2021/0022711 A1* 1/2021 Jiang .................... A61B 8/54
2021/0085287 A1* 3/2021 Hennersperger ......... A61B 8/54
2022/0059227 A1* 2/2022 Park ..................... G16H 50/20

* cited by examiner

METHODS AND SYSTEMS FOR SHEAR WAVE ELASTOGRAPHY

FIELD

Embodiments of the subject matter disclosed herein relate to ultrasound imaging, and more specifically to shear wave elastography for ultrasound imaging.

BACKGROUND

Medical diagnostic ultrasound is an imaging modality that employs ultrasound waves to probe the internal structures of a body of a patient and produce a corresponding image. For example, an ultrasound probe comprising a plurality of transducer elements emits ultrasonic pulses which reflect or echo, refract, or are absorbed by structures in the body. The ultrasound probe then receives reflected echoes, which are processed into an image. Such transducer elements of the ultrasound probe typically include electromechanical elements capable of converting electrical energy into mechanical energy for transmission of ultrasonic waves into patient tissue and mechanical energy back into electrical energy when the reflected ultrasonic waves reach the transducers.

Shear wave elastography provides a quantitative ultrasound imaging mode, wherein shear waves propagate through tissue, causing transient displacements. The ultrasound probe can measure, via ultrasonic pulses or waves propagating perpendicular to the shear waves, the velocity of these transient displacements, which are related to the elastic properties of the tissue. A shear-wave image or elastic image formed from such measurements thus depicts the elasticity of the tissue.

BRIEF DESCRIPTION

In one embodiment, a method comprises acquiring, with an ultrasound transducer of a scanning apparatus during an ultrasound scan of a patient, an ultrasound image, detecting, with an artificial intelligence model, a region of interest within the ultrasound image including a possible tumor, acquiring, with the ultrasound transducer, an elastic image of tissue within the region of interest, and displaying, with a display device, the elastic image. In this way, shear wave elastography may be automatically targeted to a region of interest, thereby reducing the processing load for the analysis and enabling a higher elasticity imaging frame rate for three-dimensional ultrasound imaging. Further, by constraining the elastography to regions of interest, the attention of a physician reviewing the ultrasound and elastic images may be directed to potential tumors. Further still, by improving the quality and accuracy of elastography, the elasticity measurements may be useful for non-invasive diagnostics and functional imaging.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
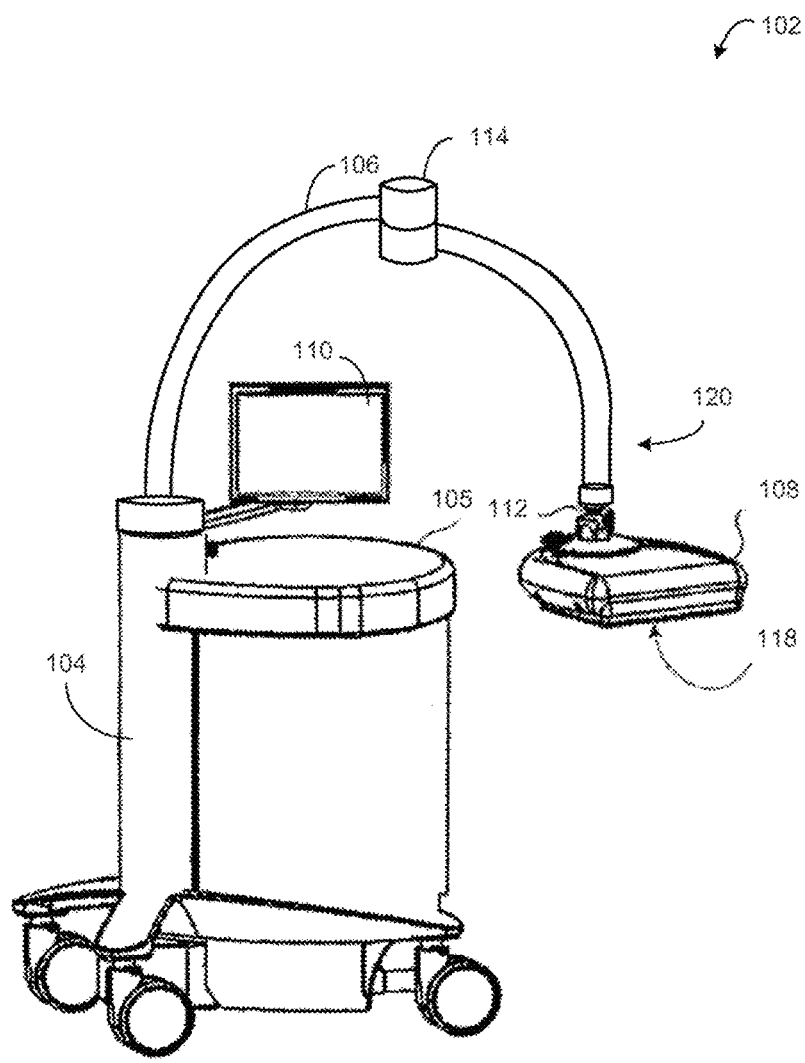
FIG. 1 shows a perspective view of a scanning apparatus according to an embodiment.
Figure 2:
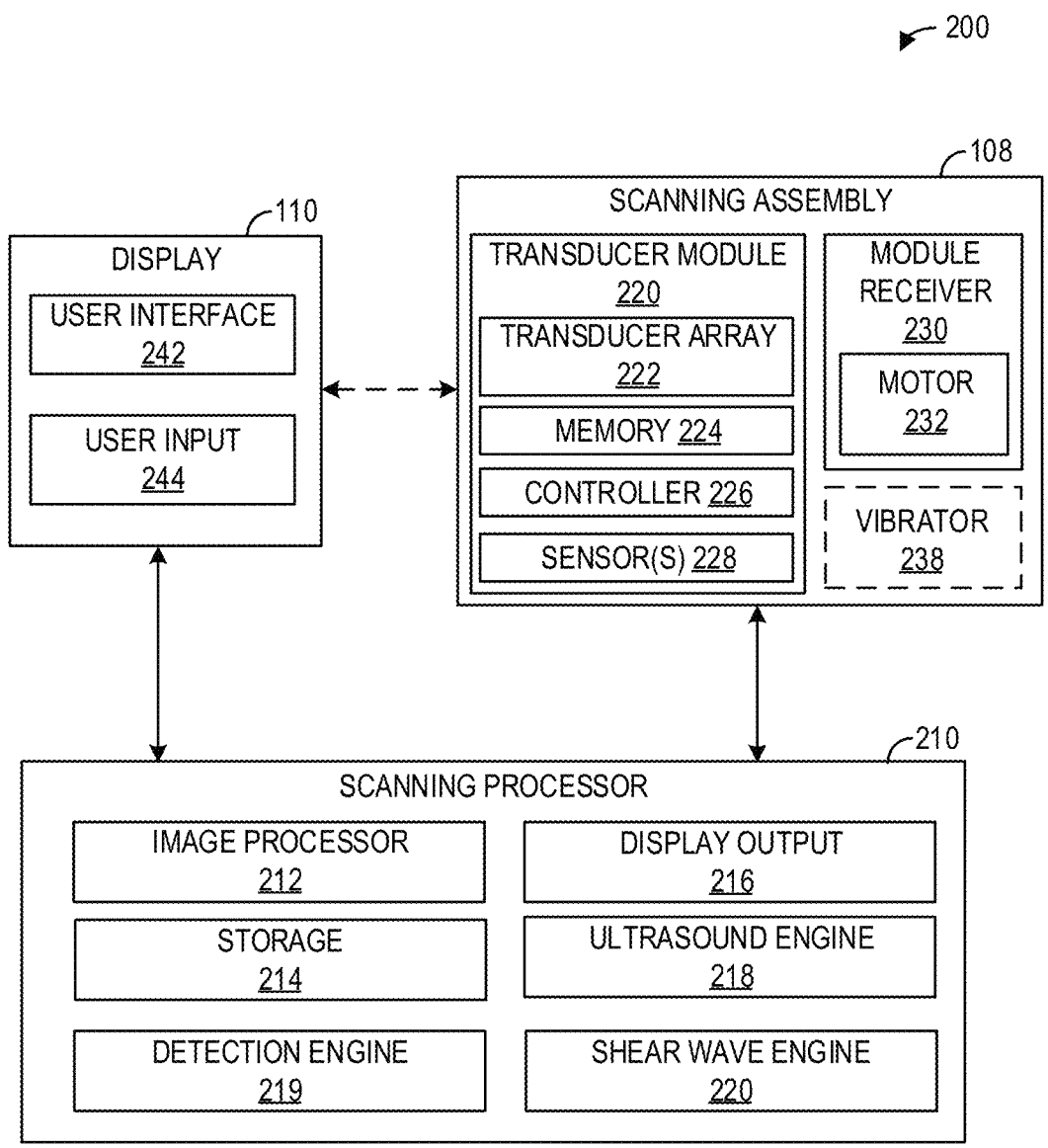
FIG. 2 shows a block schematic diagram of various system components of a scanning apparatus according to an embodiment.
Figure 3:
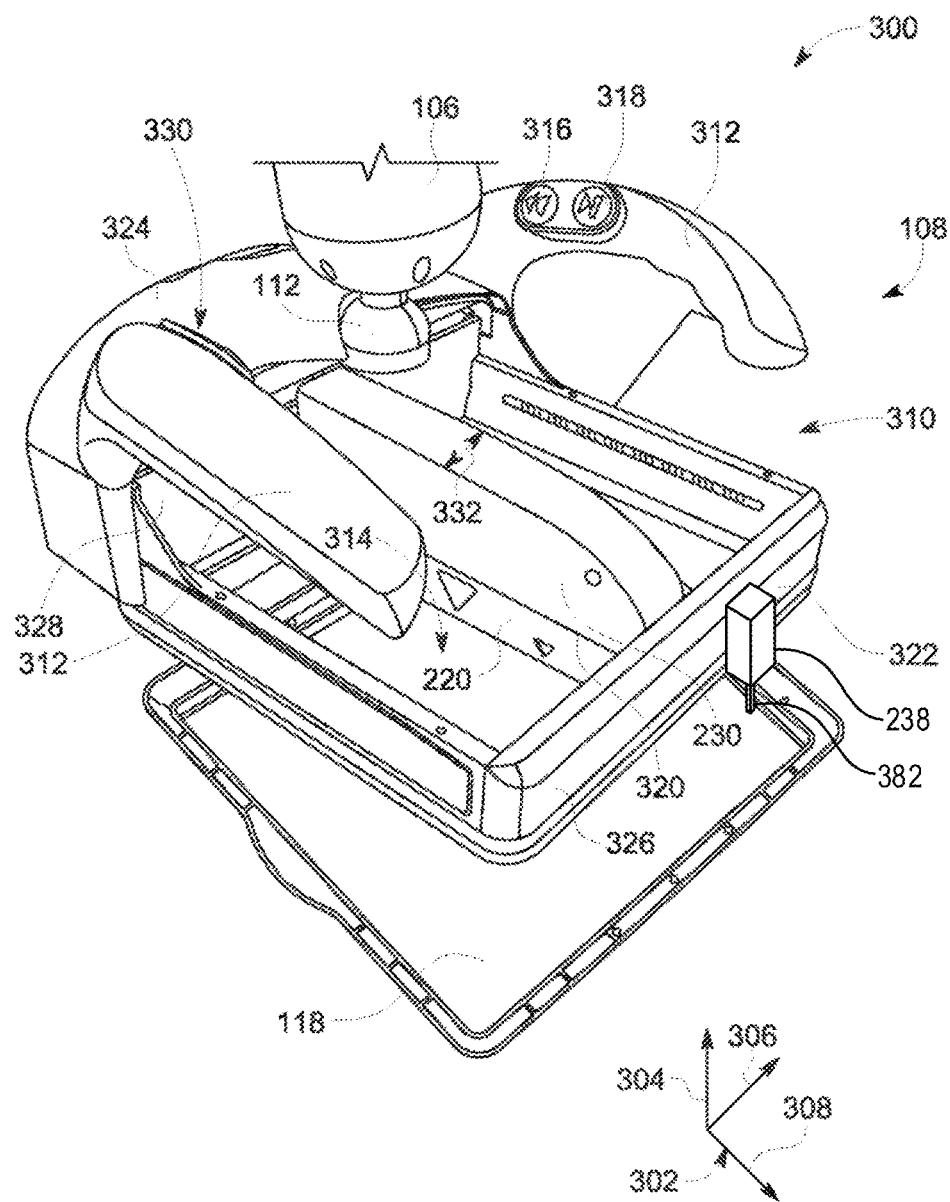
FIG. 3 shows a scanning assembly of a scanning apparatus according to an embodiment.
Figure 5:
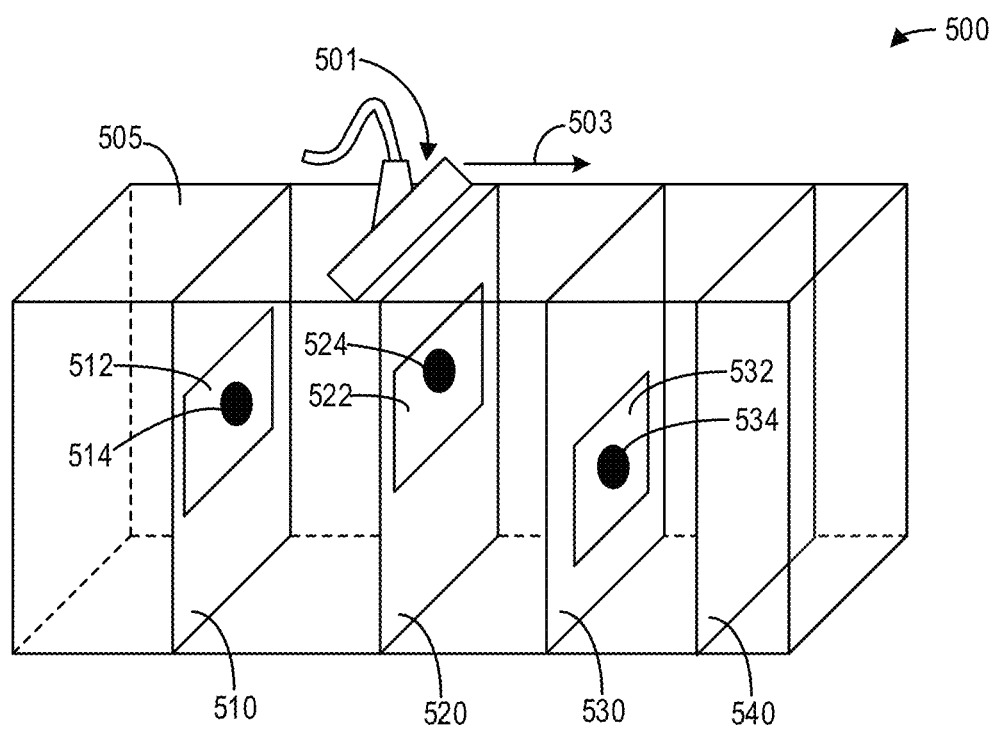
FIG. 5 shows a block diagram illustrating an example detection of a region of interest in different slices of a volume according to an embodiment.
Figure 6:
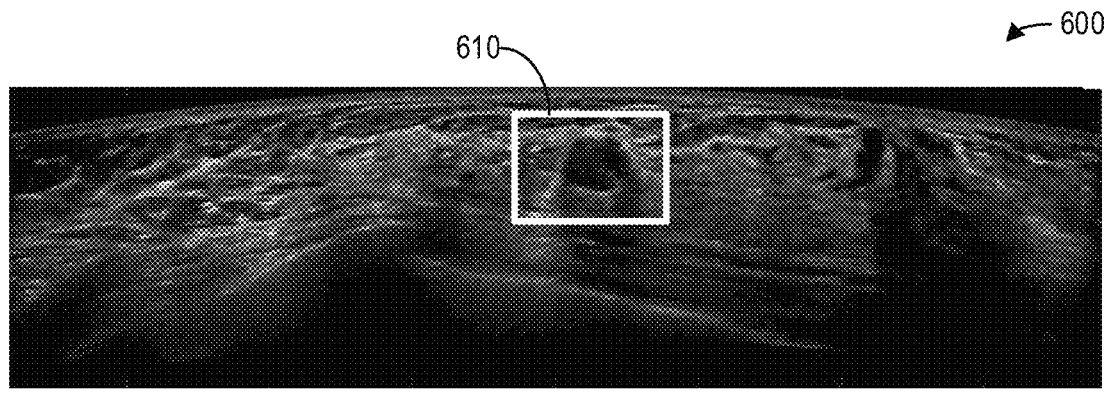
FIG. 6 shows an example first B-mode image corresponding to a first slice of a volume with a first region of interest for elastic imaging according to an embodiment.
Figure 7:
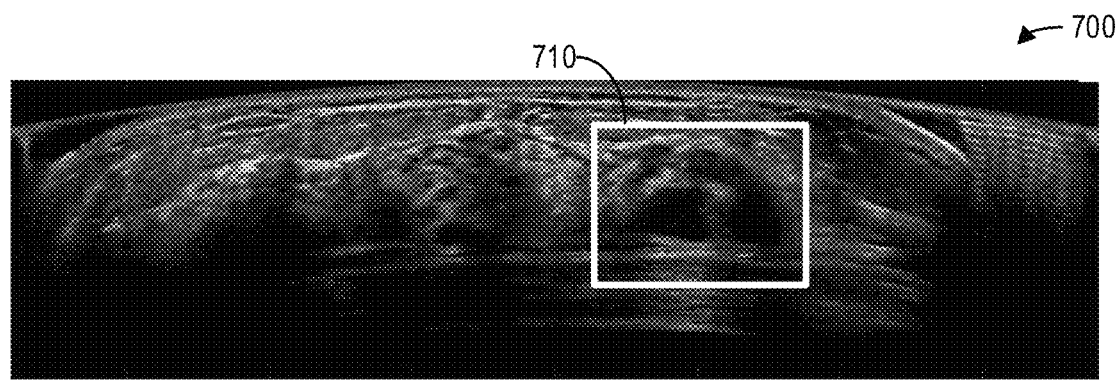
FIG. 7 shows an example second B-mode image corresponding to a second slice of a volume with a second region of interest for elastic imaging according to an embodiment.
Figure 8:
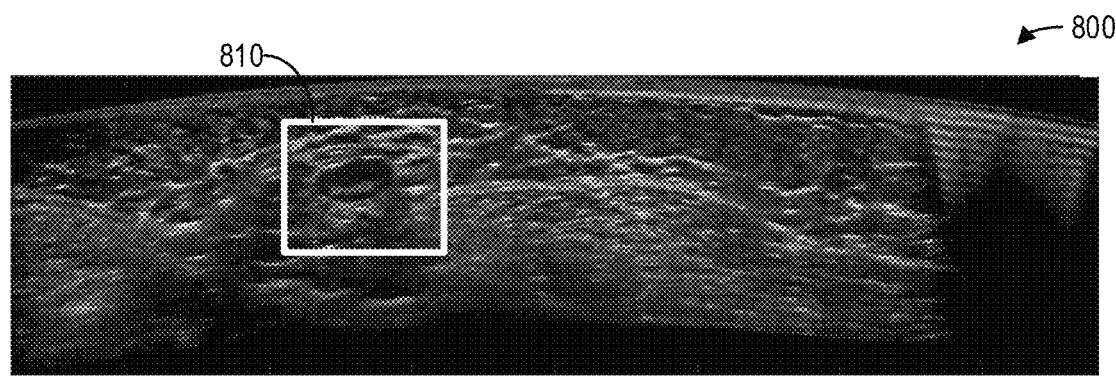
FIG. 8 shows an example third B-mode image corresponding to a third slice of a volume with a third region of interest for elastic imaging according to an embodiment.
Figure 9:
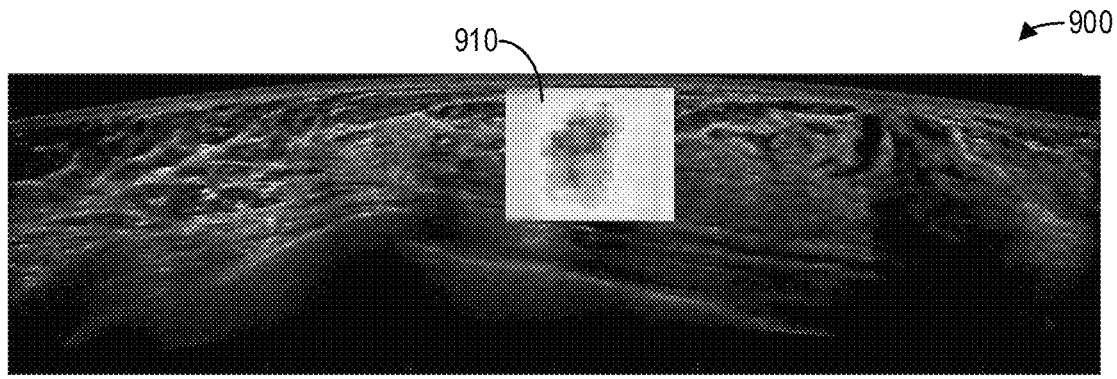
FIG. 9 shows the example first B-mode image of FIG. 6 with a corresponding first elastic image superimposed on the first region of interest according to an embodiment.
Figure 10:
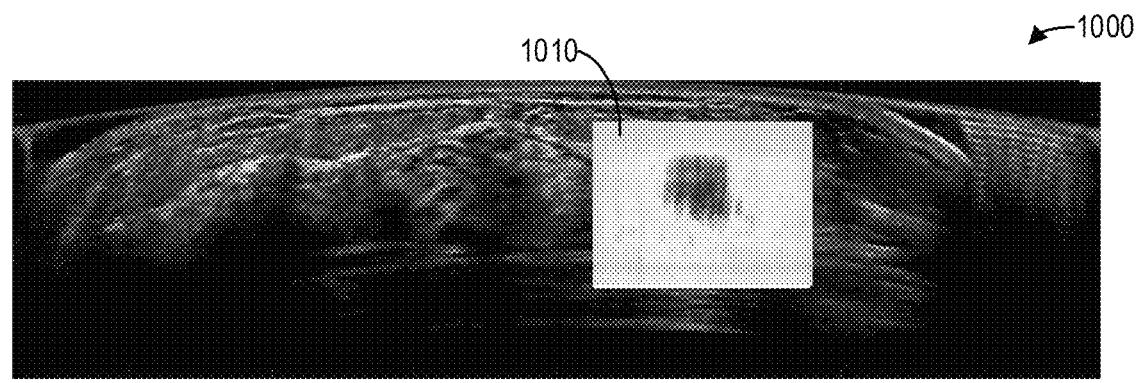
FIG. 10 shows the example second B-mode image of FIG. 7 with a corresponding second elastic image superimposed on the second region of interest according to an embodiment.
Figure 11:
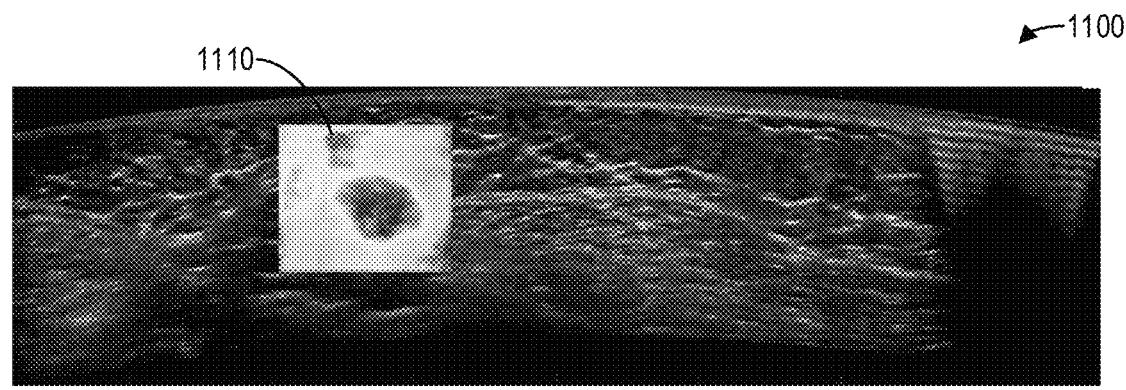
FIG. 11 shows the example third B-mode image of FIG. 8 with a corresponding third elastic image superimposed onto the third region of interest according to an embodiment.

The following description relates to various embodiments of ultrasound imaging. In particular, systems and methods for shear wave elastography are provided. FIGS. 1-3 illustrate an example full-field breast ultrasound (FFBU) scanning apparatus. A method for ultrasound imaging, such as the method depicted in FIG. 4, includes detecting a possible tumor within an ultrasound image, and performing shear wave elasticity analysis at a region of interest including the possible tumor. By targeting the shear wave elasticity analysis or elastography to specific regions of interest, the volume of data being analyzed is much smaller than the volume being ultrasound imaged, as depicted in FIG. 5. FIGS. 6-8 depict example ultrasound images with regions of interest automatically determined by an AI model, while FIGS. 9-11 depict the ultrasound images of FIGS. 6-8 with elastic images acquired via shear wave elastography superimposed thereon.

FIG. 1 illustrates a perspective view of a full-field breast ultrasound (FFBU) scanning apparatus 102, hereinafter also referred to generally as scanning apparatus 102, according to an embodiment. Scanning apparatus 102 comprises a frame 104, an ultrasound processor housing 105 that contains an ultrasound processor, a movable and adjustable support arm 106 (e.g., adjustable arm) including a hinge joint 114, a compression/scanning assembly 108 connected to a first end 120 of the adjustable arm 106 via a ball-and-socket connector (e.g., ball joint) 112, and a display 110 connected to the frame 104. The display 110 is coupled to the frame 104 at an interface where the adjustable arm 106 enters into the frame 104. As a result of being directly coupled to the frame 104 and not to the adjustable arm 106, the display 110 does not affect a weight of the adjustable arm 106 and a counterbalance mechanism of the adjustable arm 106. In one example, the display 110 is rotatable in a horizontal and lateral direction (e.g., rotatable around a central axis of the frame 104), but not vertically movable. In an alternate example, the display 110 may also be vertically movable. While FIG. 1 depicts the display 110 coupled to the frame 104, in other examples the display 110 may be coupled to a different component of the scanning apparatus 102, such as coupled to the ultrasound processor housing 105, or located remotely from the scanning apparatus 102.

In one embodiment, the adjustable arm 106 is configured and adapted such that the compression/scanning assembly 108 is either (i) neutrally buoyant in space, or (ii) has a light net downward weight (e.g., 1-2 kg) for breast compression, while allowing for easy user manipulation. In alternate embodiments, the adjustable arm 106 is configured such that the compression/scanning assembly 108 is neutrally buoyant in space during positioning the scanner on the patient's tissue. Then, after positioning the compression/scanning assembly 108, internal components of the scanning apparatus 102 may be adjusted to apply a desired downward weight for breast compression and increased image quality. In one example, the downward weight (e.g., force) may be in a range of 2-11 kg.

As introduced above, the adjustable arm 106 includes a hinge joint 114. The hinge joint 114 bisects the adjustable arm 106 into a first arm portion and a second arm portion. The first arm portion is coupled to the compression/scanning assembly 108 and the second arm portion is coupled to the frame 104. The hinge joint 114 allows the second arm portion to rotate relative to the second arm portion and the frame 104. For example, the hinge joint 114 allows the compression/scanning assembly 108 to translate laterally and horizontally, but not vertically, with respect to the second arm portion and the frame 104. In this way, the compression/scanning assembly 108 may rotate toward or away from the frame 104. However, the hinge joint 114 is configured to allow the entire adjustable arm 106 (e.g., the first arm portion and the second arm portion) to move vertically together as one piece (e.g., translate upwards and downwards with the frame 104).

The compression/scanning assembly 108 comprises an at least partially conformable membrane 118 in a substantially taut state for compressing a breast, the membrane 118 having a bottom surface contacting the breast while a transducer is swept across a top surface thereof to scan the breast. In one example, the membrane is a taut fabric sheet.

Optionally, the adjustable arm may comprise potentiometers (not shown) to allow position and orientation sensing for the compression/scanning assembly 108, or other types of position and orientation sensing (e.g., gyroscopic, magnetic, optical, radio frequency (RF)) can be used. Within ultrasound processor housing 105 may be provided a fully functional ultrasound engine for driving an ultrasound transducer and generating volumetric breast ultrasound data from the scans in conjunction with the associated position and orientation information. In some examples, the volumetric scan data may be transferred to another computer system for further processing using any of a variety of data transfer methods known in the art, or the volumetric scan data may be processed by the ultrasound engine. A general purpose computer/processor, which may be integrated with the ultrasound engine, may also be provided for general user interfacing and system control. The general purpose computer may be a self-contained stand-alone unit, or may be remotely controlled, configured, and/or monitored by a remote station connected across a network.

FIG. 2 is a block diagram 200 schematically illustrating various system components of the scanning apparatus 102, including the scanning assembly 108, display 110, and a scanning processor 210. Scanning processor 210 may be included within ultrasound processor housing 105 of the scanning apparatus 102 in one example. As illustrated in the embodiment of FIG. 2, the scanning assembly 108, display 110, and scanning processor 210 are separate components in communication with each other; however, in some embodiments, one or more of the components may be integrated (e.g., the display and scanning processor may be included in a single component).

Referring first to the scanning assembly 108, it comprises a transducer module 220 connected to a module receiver 230. The module receiver 230 may be positioned within a housing (attached to the arm 106 of the scanning apparatus, for example) that is configured to remain stationary during scanning, while the module receiver 230 is configured to translate with respect to the housing during scanning. In order to automatically translate with respect to the housing during scanning, the module receiver includes a motor 232 activated by the scanning processor 210, as explained below.

The transducer module 220 comprises a transducer array 222 of transducer elements, such as piezoelectric elements, that convert electrical energy into ultrasound waves and then detect the reflected ultrasound waves. The transducer module 220 is configured to be removably coupled with the module receiver 230 via a connection 234. The connection 234 may include complementary connectors on the transducer module and module receiver (e.g., a first connector on the transducer module that is configured to connect with a second connector on the module receiver) in order to establish both a mechanical connection and an electrical connection between the module receiver and the transducer module.

The transducer module 220 may further include a memory 224. Memory 224 may be a non-transitory memory configured to store various parameters of the transducer module 220, such as transducer usage data (e.g., number of scans performed, total amount of time spent scanning, etc.), as well as specification data of the transducer (e.g., number of transducer array elements, array geometry, etc.) and/or identifying information of the transducer module 220, such as a serial number of the transducer module. Memory 224 may include removable and/or permanent devices, and may include optical memory, semiconductor memory, and/or magnetic memory, among others. Memory 224 may include volatile, non-volatile, dynamic, static, read/write, read-only, random-access, sequential-access, and/or additional memory. In an example, memory 224 may include RAM. Additionally or alternatively, memory 224 may include EEPROM.

Memory 224 may store non-transitory instructions executable by a controller or processor, such as controller 226, to carry out one or more methods or routines as described herein below. Controller 226 may receive output from various sensors 228 of the transducer module 220 and trigger actuation of one or more actuators and/or communicate with one or more components in response to the sensor output. Sensors 228 may include one or more pressure sensors and/or one or more temperature sensors. During scanning, the pressure across the scanning assembly 108 may be measured by the pressure sensors, and if the pressure distribution across the transducer module is not equal, a user may be notified (via user interface 242 of display 110, for example) to reposition the scanning assembly 108. Further, in some embodiments, to initiate scanning, motor 232 may be activated via a signal from controller 226. However, in other embodiments, motor 232 may be activated via a signal from a separate scanning processor 210, explained below.

Scanning assembly 108 may be in communication with scanning processor 210, to send raw scanning data to an image processor, for example. Additionally, data stored in memory 224 and/or output from sensors 228 may be sent to scanning processor 210 in some examples. Further, various actions of the scanning assembly 108 (e.g., translation of the module receiver 230, activation of the transducer elements, etc.) may be initiated in response to signals from the scanning processor 210. Scanning assembly 108 may optionally communicate with display 110, in order to notify a user to reposition the scanning assembly, as explained above, or to receive information from a user (via user input 224), for example.

Scanning assembly 108 may further include a vibrator 238, in some examples. The vibrator 238 comprises an external vibrator configured to generate shear waves into tissue of the subject being imaged during shear wave elastography. For example, the vibrator 238 may comprise a motor mounted to the scanning assembly 108, and further may be fixed or moveable relative to the transducer module 220. As discussed herein, the position of a tumor may be automatically detected within images, and the vibrator 238 may be automatically positioned within the scanning assembly 108 in order to generate shear waves towards the detected position of the tumor. Additionally or alternatively, the amplitude and/or frequency of the shear wave(s) generated by the vibrator 238 for shear wave elastography may be varied according to the detected position of the tumor. Further, during shear wave elastography, the transducer module 220 is controlled to measure the response of the tissue to the shear wave(s) generated by the vibrator 238. For example, the transducer module 220 is controlled with an acoustic beam sequence designed for shear wave detection, and specifically may target a region of interest including the detected tumor, so that the transducer module 220 may measure elasticity/viscosity of the tissue within the region of interest and reconstruct an elastic image.

Turning now to scanning processor 210, it includes an image processor 212, storage 214, display output 216, and ultrasound engine 218. Ultrasound engine 218 may drive activation of the transducer elements of the transducer array 222 of transducer module 220 and, in some embodiments, may activate motor 232. Further, ultrasound engine 218 may receive raw image data (e.g., ultrasound echoes) from the scanning assembly 108. The raw image data may be sent to image processor 212 and/or to a remote processor (via a network, for example) and processed to form a displayable image of the tissue sample. It is to be understood that the image processor 212 may be included with the ultrasound engine 218 in some embodiments.

Information may be communicated from the ultrasound engine 218 and/or image processor 212 to a user of the scanning apparatus 102 via the display output 216 of the scanning processor 210. In one example, the user of the scanning apparatus may include an ultrasound technician, nurse, or physician such as a radiologist. For example, processed images of the scanned tissue may be sent to the display 110 via the display output 216. In another example, information relating to parameters of the scan, such as the progress of the scan, may be sent to the display 110 via the display output 216. The display 110 may include a user interface 242 configured to display images or other information to a user. Further, user interface 242 may be configured to receive input from a user (such as through user input 244) and send the input to the scanning processor 210. User input 244 may be a touch screen of the display 110 in one example. However, other types of user input mechanisms are possible, such as a mouse, keyboard, etc.

Scanning processor 210 may further include storage 214. Similar to memory 224, storage 214 may include removable and/or permanent devices, and may include optical memory, semiconductor memory, and/or magnetic memory, among others. Storage 214 may include volatile, non-volatile, dynamic, static, read/write, read-only, random-access, sequential-access, and/or additional memory. Storage 214 may store non-transitory instructions executable by a controller or processor, such as ultrasound engine 218 or image processor 212, to carry out one or more methods or routines as described herein below. Storage 214 may store raw image data received from the scanning assembly 108, processed image data received from image processor 212 or a remote processor, and/or additional information.

Scanning processor 210 may further include a detection engine 219. The detection engine 219 comprises one or more artificial intelligence or machine learning models configured to detect lesions or tumors within an ultrasound image. For example, the detection engine 219 may comprise one or more artificial intelligence models such as deep learning models or machine learning models that are trained or otherwise configured to detect lesions or tumors within an ultrasound image, and output a size and position of a region of interest that includes the potential lesion or tumor within the ultrasound image. For the absence of a potential tumor, the detection engine 219 may output a null region of interest (e.g., a region of interest without a size or a position) to indicate the absence of a potential tumor, or in some examples the detection engine 219 may output an explicit classification that the ultrasound image does not contain a potential tumor.

The scanning processor 210 may further include a shear wave engine 220 configured to control the scanning module 220 and/or the vibrator 238 to perform shear wave elastography based on the output of the detection engine 219. That is, the detection engine 219 detects a possible tumor or lesion in an ultrasound image and outputs a region of interest bounding the position of the suspected tumor. The shear wave engine 220 controls the transducer module 220 and/or the vibrator 238 to perform shear wave elastography within the region of interest output by the detection engine 219. For example, the shear wave engine 220 may control the transducer module 220 to generate shear waves towards the tissue within the region of interest. As another example, the shear wave engine 220 may control the vibrator 238 to generate shear waves towards the tissue within the region of interest. Further, the shear wave engine 220 may control the transducer module 220 to acquire elastic images that depict the response of the tissue to the shear waves within the region of interest, as described further herein below.

FIG. 3 shows a schematic 300 of an isometric view of the scanning assembly 108 coupled to the adjustable arm 106. The schematic 300 includes a coordinate system 302 including a vertical axis 304, horizontal axis 306, and a lateral axis 308.

The scanning assembly 108 includes a housing 310, the transducer module 220, and the module receiver 230. The housing 310 includes a frame 322 and a handle portion 324, the handle portion including two handles 312. The two handles 312 are opposite one another across a lateral axis of the scanning assembly 108, the lateral axis centered at the adjustable arm 106 and defined with respect to the lateral axis 308. The frame 322 is rectangular-shaped with an interior perimeter of the frame 322 defining an opening 314. The opening 314 provides a space (e.g., void volume) for translating the module receiver 230 and the transducer module 220 during a scanning procedure. In another example, the frame 322 may be another shape, such as a square with a square-shaped opening 314. Additionally, the frame 322 has a thickness defined between the interior perimeter and an exterior perimeter of the frame 322.

The frame 322 includes four sets of side walls (e.g., the set including an interior side wall and an exterior side wall, the interior side walls defining the opening 314). Specifically, the frame 322 includes a front side wall 326 and a back side wall 328, the back side wall 328 directly coupled to the handle portion 324 of the housing 310 and the front side wall 326 opposite the back side wall 328 with respect to the horizontal axis 306. The frame 322 further includes a right side wall and a left side wall, the respective side walls opposite from one another and both in a plane defined by the vertical axis 304 and the lateral axis 308.

The frame 322 of the housing 310 further includes a top side and a bottom side, the top side and bottom side defined relative to the vertical axis 304. The top side faces the adjustable arm 106. A membrane 118 is disposed across the opening 314. More specifically, the membrane 118 is coupled to the bottom side of the frame 322. In one example, the membrane 118 is a membranous sheet maintained taut across the opening 314. The membrane 118 may be a flexible but non-stretchable material that is thin, water-resistant, durable, highly acoustically transparent, chemically resistant, and/or biocompatible. As discussed above, the bottom surface of the membrane 118 may contact a tissue (e.g., such as a breast) during scanning and a top surface of the membrane 118 may at least partially contact the transducer module 220 during scanning. As shown in FIG. 3, the membrane 118 is permanently coupled to a hard-shell clamping portion 119 around a perimeter of the membrane 118. The clamping portion 119 couples to the bottom side of the frame 322. In one example, the clamping portion 119 may snap to a lip on the bottom side of the frame 322 of the housing 310 such that the membrane 118 does not become uncoupled during scanning but is still removably coupled to the frame 322. As discussed further herein with respect to FIGS. 4-9, the membrane 118 may not be permanently coupled to a hard-shell clamping portion 119, and thus the membrane 118 may not couple to the frame 322 via the hard-shell clamping portion 119. Instead, the membrane 118 may be directly and removably coupled to the frame 322.

The handle portion 324 of the housing 310 includes two handles 312 for moving the scanning assembly 108 in space and positioning the scanning assembly 108 on a tissue (e.g., on a patient). In alternate embodiments, the housing 310 may not include handles 312. In one example, the handles 312 may be formed as one piece with the frame 322 of the housing 310. In another example, the handles 312 and the frame 322 may be formed separately and then mechanically coupled together to form the entire housing 310 of the scanning assembly 108.

As shown in FIG. 3, the scanning assembly 108 is coupled to the adjustable arm 106 through a ball joint 112 (e.g., ball-and-socket connector). Specifically, a top, domed portion of the handle portion 324 is coupled to the ball joint 112. The top portion of the handle portion 324 includes a concave depression forming a socket which a ball of the ball joint 112 fits into. The ball joint 112 is movable in multiple directions. For example, the ball joint 112 provides rotational movement of the scanning assembly relative to the adjustable arm 106. The ball joint 112 includes a locking mechanism for locking the ball joint 112 in place and thereby maintaining the scanning assembly 108 stationary relative to the adjustable arm 106.

Additionally, as shown in FIG. 3, the handles 312 of the handle portion 324 include buttons for controlling scanning and adjusting the scanning assembly 108. Specifically, a first handle of the handles 312 includes a first weight adjustment button 316 and a second weight adjustment button 318. The first weight adjustment button 316 may decrease a load applied to the scanning assembly 108 from the adjustable arm 106. The second weight adjustment button 318 may increase the load applied to the scanning assembly 108 from the adjustable arm 106. Increasing the load applied to the scanning assembly 108 may increase an amount of pressure and compression applied to the tissue on which the scanning assembly 108 is placed. Further, increasing the load applied to the scanning assembly increases the effective weight of the scanning assembly on the tissue to be scanned. In one example, increasing the load may compress the tissue, such as a breast, of a patient. In this way, varying amounts of pressure (e.g., load) may be applied consistently with the scanning assembly 108 during scanning in order to obtain a quality image with the transducer module 220.

Before a scanning procedure, a user (e.g., ultrasound technician or physician) may position the scanning assembly 108 on a patient or tissue. Once the scanning assembly 108 is positioned correctly, the user may adjust the weight of the scanning assembly 108 on the patient (e.g., adjust the amount of compression) using the first weight adjustment button 316 and/or the second weight adjustment button 318. A user may then initiate a scanning procedure with additional controls on the handle portion 324 of the housing 310. For example, as shown in FIG. 3, a second handle of the handles 312 includes two additional buttons 330 (not individually shown). The two additional buttons 330 may include a first button to initiate scanning (e.g., once the scanning assembly has been placed on the tissue/patient and the amount of compression has been selected) and a second button to stop scanning. In one example, upon selecting the first button, the ball joint 112 may lock, thereby stopping lateral and horizontal movement of the scanning assembly 108.

The module receiver 230 is positioned within the housing 310. Specifically, the module receiver 230 is mechanically coupled to a first end of the housing 310 at the back side wall 328 of the frame 322, the first end closer to the adjustable arm 106 than a second end of the housing 310. The second end of the housing 310 is at the front side wall 326 of the frame 322. In one example, the module receiver 230 is coupled to the first end via a protrusion of the module receiver 230, the protrusion coupled to a motor 230, the protrusion coupled to a motor (e.g., motor 232 described with reference to FIG. 2 above) of the module receiver 230.

As described above, the housing 310 is configured to remain stationary during scanning. In other words, upon adjusting a weight applied to the scanning assembly 108 through the adjustable arm 106 and then locking the ball joint 112, the housing 310 may remain in a stationary position without translating in the horizontal or lateral directions. However, the housing 310 may still translate vertically with vertical movement of the adjustable arm 106.

Conversely, the module receiver 230 is configured to translate with respect to the housing 310 during scanning. As shown in FIG. 3, the module receiver 230 translates horizontally, along the horizontal axis 306, with respect to the housing 310. The motor of the module receiver 230 may slide the module receiver 230 along a top surface of the first end of the housing 310.

The transducer module 220 is removably coupled with the module receiver 230. As a result, during scanning, the transducer module 220 translates horizontally with the module receiver 230. During scanning, transducer module 220 sweeps horizontally across the breast under motor control of the module receiver 230 while a contact surface of the transducer module 220 is in contact with the membrane 118. The transducer module 220 and the module receiver 230 are coupled together at a module interface 320. The module receiver 230 has a width 332 which is the same as a width of the transducer module 220. In alternate embodiments, the width 332 of the module receiver may not be the same as the width of the transducer module 220. In some embodiments, the module interface 320 includes a connection 234 between the transducer module 220 and the module receiver 230, the connection 234 including a mechanical and electrical connection.

As depicted in FIG. 3, the vibrator 238 may be coupled to the frame 322 of the scanning assembly 108. The vibrator 238 may include a vibrating arm 382 extending therefrom that may be in physical contact with the skin of the subject being imaged, in some examples, such that the vibrator 238 may generate shear waves into the subject via the vibrating arm 382. The position of the vibrator 238 may be adjusted manually or automatically relative to the transducer module 220, for example via a motor (not shown), based on detected position of suspected tumors to further improve the elastography measurements.

Figure 4:
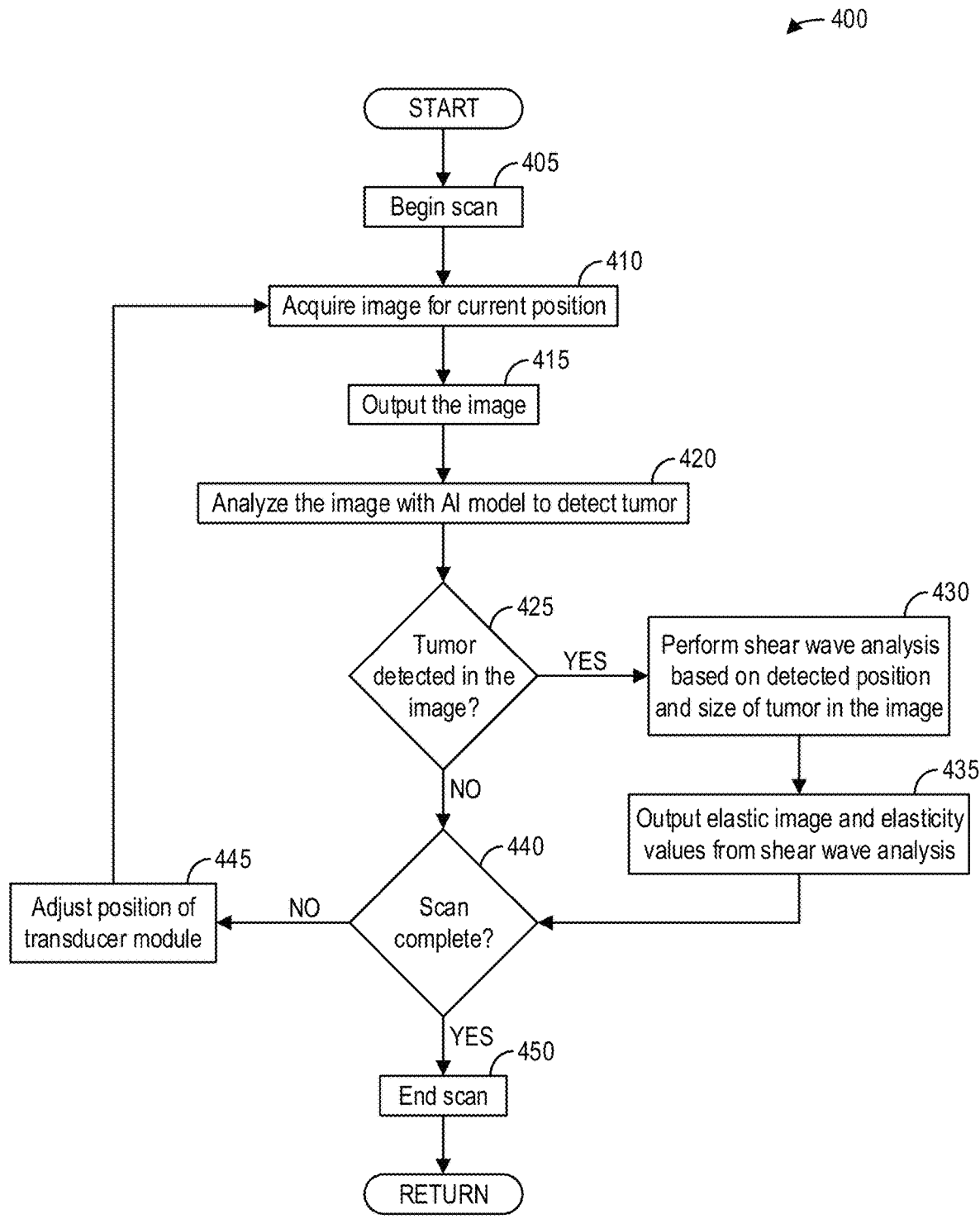
FIG. 4 shows a high-level flow chart illustrating an example method for ultrasound imaging with shear wave elastography according to an embodiment.

FIG. 4 shows a high-level flow chart illustrating an example method 400 for ultrasound imaging with shear wave elastography according to an embodiment. In particular, method 400 relates to selectively performing shear wave elastography at regions automatically detected by an AI model for each slice of a volume being imaged. By limiting the shear wave analysis to such detected regions, the amount of data being processed and calculated for elastography is reduced, thereby improving the elasticity imaging frame rate. Method 400 is described with regard to the systems and components of FIGS. 1-3, though it should be appreciated that the method 400 may be implemented with other systems and components without departing from the scope of the present disclosure. Method 400 may be implemented as executable instructions in non-transitory memory and executed by a processor, such as the memory 224 and controller 226 of the transducer module 220 and/or the storage 214 and image processor 212 of the scanning processor 210.

Method 400 begins at 405. At 405, method 400 begins a scan. In particular, method 400 begins a scan of a volume of interest of an imaging subject, such as a patient. The volume of interest may comprise, for example, a breast of the patient, or another portion of the body of the patient. The scan may comprise an imaging session, with an ultrasound imaging system or scanning apparatus such as the full-field breast ultrasound (FFBU) scanning apparatus 102, during which the volume of interest is scanned or imaged by the scanning apparatus. During the scan, method 400 may control a scanning assembly of the scanning apparatus, such as the scanning assembly 108, to acquire ultrasound images of the volume of interest. Specifically, method 400 may control the scanning assembly 108 to acquire a plurality of two-dimensional images or slices throughout the three-dimensional volume of interest. For example, during the scan, method 400 controls, via the module receiver 230, the position of the transducer module 220, to a plurality of positions relative to the housing of the scanning assembly 108, and further controls the transducer module 220 to acquire at least one ultrasound image for each position while the transducer module 220 is at the position. Thus, at the beginning of the scan, method 400 may initialize the scan by adjusting the position of the transducer module 220, via the module receiver 230, to an initial position relative to the housing of the scanning assembly 108.

At 410, method 400 acquires an image at a current position. For example, method 400 may control the transducer module 220 to acquire a B-mode or grayscale ultrasound image at the current position of the transducer module 220. After acquiring the image, method 400 continues to 415. At 415, method 400 outputs the image, for example, to a display device such as the display 110. The image may be displayed via the display 110 in a graphical user interface, for example.

Additionally or alternatively, method 400 may output the image to a detection engine, such as detection engine 219, configured with an AI model. At 420, method 400 analyzes the image with an AI model to detect a tumor. To that end, method 400 may input the image to the AI model of the detection engine 219. The AI model, which may comprise a deep learning algorithm such as a convolutional neural network, is trained to classify or identify regions of interest containing a potential lesion or tumor. The AI model thus outputs a classification, for example, of whether a tumor is potentially visible in the image, and if a tumor is potentially visible in the image, the AI model further outputs an indication of a region of interest in the image containing the tumor. The indication of the region of interest may include a specification of the position and size of the region of interest within the image. As another example, the AI model may simply output the current slice index position along with the position and size of a region of interest potentially including a tumor. In such an example, the classification of no potential tumor may be determined from the output of a null result for the position and size of the region of interest.

Continuing at 425, method 400 determines whether a tumor was detected in the image. A potential tumor was detected in the image if the AI model outputs a size and position of a region of interest, for example as discussed hereinabove.

If a tumor was detected in the image ("YES"), method 400 continues to 430. At 430, method 400 performs shear wave analysis based on the detected position and size of the tumor in the image. For example, method 400 controls the scanning assembly 108 to scan the region of interest corresponding to the detected position and size of the tumor in the image according to shear wave elastography. To that end, method 400 controls the scanning assembly 108 to generate shear waves within the patient to induce distortion of the tissue, and then further to image the response of the tissue to the shear waves.

To control the scanning assembly 108 to generate shear waves, method 400 may control the transducer module 220 or the vibrator 238. For example, method 400 may control the transducer module 220 to generate a focused acoustic plane wave towards the region of interest, such that shear waves or a push is induced in the tissue by acoustic radiation force. As another example, method 400 may control an external vibrator such as the vibrator 238 to generate shear waves in the tissue. In some examples, method 400 may adjust the position of the vibrator 238 based on one or more of the current slice index position and the position and size of the region of interest. For example, method 400 may align the vibrator 238 with the current slice position and/or the position and size of the region of interest prior to controlling the vibrator 238 to generate the shear waves. Additionally or alternative, method 400 may control the vibrator 238 to generate shear waves based on the size and position of the region of interest, for example by increasing or decreasing the amplitude or otherwise adjusting the shape of the shear waves generated by the vibrator 238 such that the shear waves reach the region of interest with a desired force. In this way, method 400 may ensure that the shear waves reach the region of interest without dissipating in the tissue prior to reaching the region of interest.

After generating the shear waves via the scanning assembly 108, method 400 further controls the scanning assembly 108 to image the response of the tissue to the shear waves. Method 400 may control the scanning assembly 108 to specifically image the response within the region of interest. For example, method 400 may control the transducer module 220 to generate ultrasonic waves towards the region of interest and to detect the echoes of the ultrasonic waves. Method 400 may thus image the tissue to track the shear waves as they travel through the tissue, and method 400 may further measure the displacement of the tissue based on the imaging to determine the response of the tissue. Method 400 may estimate the shear modulus and/or construct tissue displacement maps based on the received echoes, and furthermore may calculate or measure the shear wave speed throughout the region of interest.

At 435, method 400 outputs an elastic image and measured elasticity values obtained from the shear wave analysis. The elastic image may comprise the tissue displacement maps or the measurements of the shear wave speed through the region of interest. The elastic image may be output, for example, via a display device such as the display 110. In particular, the elastic image may be superimposed on the ultrasound image acquired at 410, and specifically the elastic image may be superimposed over the region of interest identified by the AI model at 420. The elastic image and the measured elasticity values may further be output to memory. Method 400 then proceeds to 440.

However, referring again to 425, if a tumor was not detected in the image ("NO"), method 400 proceeds to 440. At 440, method 400 determines whether the scan is complete. The scan may be complete when the transducer module 220 is at a final position relative to the scanning assembly 108. For example, during the scan, the transducer module 220 acquires at least an ultrasound image at each position of a plurality of positions relative to the scanning assembly 108. The plurality of positions may be determined, for example, based on a volume of interest to be scanned, such that the range of the plurality of positions corresponds to the range (e.g., width) of the volume of interest. Once the transducer module 220 is at the final position, all two-dimensional slices or ultrasound images for the volume of interest have been acquired, and so the scan may be considered complete. If not all slices have been acquired, then the scan is not complete.

If the scan is not complete ("NO"), method 400 continues to 445. At 445, method 400 adjusts the position of the transducer module to a next position. For example, method 400 controls the motor 232 of the module receiver 230 to adjust the position of the transducer module 220 relative to the scanning assembly 108 to the next position in the plurality of positions described hereinabove. Method 400 then returns to 410, where method 400 acquires an image at the updated position. Method 400 thus continues acquiring images, analyzing the images to detect tumors, and selectively performing shear wave analysis when tumors are detected, until method 400 determines that the scan is complete ("YES") at 440. Method 400 then returns.

Once method 400 determines that the scan is complete, method 400 proceeds from 440 to 450. At 450, method 400 ends the scan. When ending the scan, method 400 may output the plurality of ultrasound images acquired at 410 as well as any elastic images and elasticity values obtained at 430 to storage, such as storage 214, and in some examples may additionally or alternatively output the images to a picture archiving and communication system (PACS) for remote storage and review. After ending the scan, method 400 returns.

To illustrate how the transducer module 220 may be re-positioned during an ultrasound scan to acquire a plurality of ultrasound images corresponding to two-dimensional slices of a volume of interest, FIG. 5 shows a block diagram illustrating an example method 500 for detecting a region of interest in different slices of a volume 505 according to an embodiment. An ultrasound probe 501, which may comprise the transducer module 220, moves in a direction 503 relative to a volume 505 being imaged by the ultrasound probe 501. The ultrasound probe 501 may acquire a plurality of images at a plurality of positions relative to the volume 505, including a first image 510, a second image 520, a third image 530, and a fourth image 540.

Each image, which may comprise a grayscale or B-mode ultrasound image, acquired via the ultrasound probe 501 thus comprises a slice of the volume 505. As discussed hereinabove, each image or image slice is analyzed with an AI model to detect a tumor in the image. As depicted, an object 514 that is likely a tumor is detected in a first region of interest 512 in the first image 510, an object 524 is detected in a second region of interest 522 in the second image 520, and an object 534 is detected in the third region of interest 532 in a third image 530. The objects 514, 524, and 534 may correspond to one or more tumors in the volume 505. As depicted, the objects 514, 524, and 534 are located in different positions in each image, and similarly the corresponding regions of interest 512, 522, and 532 have different positions and sizes relative to each image. It should be appreciated that while three images 510, 520, and 530 are shown, a plurality of images including more than three images may be acquired for the volume 505.

Further, while each of the images 510, 520, and 530 are depicted as including identified objects 514, 524, and 534 within identified regions of interest 512, 522, and 532 respectively, it should be appreciated that such objects and regions of interest may not be identified in each image or slice acquired by the ultrasound probe 501 in the volume 505. For example, no object of interest or region of interest is detected by the AI model in the fourth image 540. As a null region of interest (i.e., an absence of a potential tumor) is detected in the fourth image 540, shear wave elastography is not performed and the ultrasound transducer 501 is not controlled to acquire an elastic image at the slice index corresponding to the fourth image 540. By automatically identifying, with a deep learning model or AI model, regions of interest including that may potentially include one or more tumors, shear wave elastography may be specifically targeted to such objects. In this way, the entire volume 505 does not need to be interrogated and imaged according to shear wave elastography, nor does each entire slice of the volume 505 need to be interrogated and imaged according to shear wave elastography. As a result, the elastography processing and calculations may be reduced, thereby enabling an improved elasticity imaging frame rate when imaging a three-dimensional volume.

As an illustrative and non-limiting example, FIGS. 6-8 show example ultrasound images corresponding to the slices of FIG. 5 wherein a potential tumor is detected according to an embodiment. For example, the ultrasound image 600 of FIG. 6 includes an ROI overlay 610 indicating a region of interest including a possible tumor. The ultrasound image 600 and the ROI overlay 610 correspond to the first image 510 and the first region of interest 512, respectively. Similarly, the ultrasound image 700 of FIG. 7 includes an ROI overlay 710 superimposed on the ultrasound image 700 and indicating a region of interest including a possible tumor. The ultrasound image 700 and the ROI overlay 710 correspond to the second image 520 and the second region of interest 612, respectively. Further, the ultrasound image 800 of FIG. 8 includes an ROI overlay 810 superimposed on the ultrasound image 800 and indicating a region of interest including a possible tumor. The ultrasound image 800 and the ROI overlay 810 correspond to the third image 530 and the third region of interest 532, respectively. As depicted, the sizes and positions of the regions of interest for the different slices are different from each other, though it should be appreciated that in some examples the sizes and positions of detected regions of interest may be similar for adjacent slices.

The ultrasound images 600, 700, and 800 may be displayed via a display device with the ROI overlays 610, 710, and 820 superimposed thereon as depicted in FIGS. 6-8. Further, based on the automatic detection of the regions of interest by an artificial intelligence model, shear wave elastography may be guided by the regions of interest for each slice wherein a potential tumor is detected.

As the approximate position of the detected tumor within each image and an appropriate region of interest forming a boundary around the detected tumor are determined based on the AI model, shear wave elastography may be tailored or focused on the ROI. For example, FIGS. 9-11 show the example ultrasound images of FIGS. 6-8 with corresponding elastic images superimposed onto the regions of interest according to an embodiment. In particular, FIG. 9 shows an ultrasound image 900 corresponding to the ultrasound image 600 with an elastic image 910 superimposed thereon, wherein the elastic image 910 is limited to the region of interest 610. That is, rather than performing shear wave analysis at all positions of the image 600, shear wave elastography is performed within the region of interest 610 to produce the elastic image 910.

Similarly, FIG. 10 shows an ultrasound image 1000 corresponding to the ultrasound image 700 with an elastic image 1010 superimposed thereon, and FIG. 11 shows an ultrasound image 1100 corresponding to the ultrasound image 800 with an elastic image 1110 superimposed thereon.

The darker regions depicted in the elastic images 910, 1010, and 1110 correspond to regions of higher stiffness or less elasticity, while lighter regions depicted in the elastic images 910, 1010, and 1110 correspond to regions of lower stiffness or higher elasticity. As cancerous tumors are generally harder than the surrounding tissue, the darker regions depicted in the elastic images 910, 1010, and 1110 may correspond to a tumor. By focusing the shear wave elastic analysis on the regions of interest that potentially contain a tumor, the quality of the elastic imaging and the quality of the elasticity measurements in general is improved. Rather than performing shear wave elastography for the entire slice, or even the entire volume, the systems and methods provided herein enable guided elastography that reduces the amount of data for elastography processing and calculations, improves shear wave elasticity imaging quality, and improves the elasticity imaging frame rate.

A technical effect of the present disclosure includes the selective interrogation of local regions, via shear waves and ultrasonic waves, within a volume of interest to measure the elasticity of tissue and detect potential lesions or tumors. Another technical effect of the disclosure includes the automatic detection of regions of interest for additional measurements. Yet another technical effect of the disclosure includes the automatic interrogation of automatically-detected regions of interest during an ultrasound scan. Another technical effect of the disclosure includes the external vibration of tissue during an ultrasound scan. Yet another technical effect of the disclosure includes the display of elastic images acquired for regions of interest superimposed onto other ultrasound images such as B-mode images.

In one embodiment, a method comprises acquiring, with an ultrasound transducer of a scanning apparatus during an ultrasound scan of a patient, an ultrasound image, detecting, with an artificial intelligence model, a region of interest within the ultrasound image including a possible tumor, acquiring, with the ultrasound transducer, an elastic image of tissue within the region of interest, and displaying, with a display device, the elastic image.

In a first example of the method, the method further comprises controlling the scanning apparatus to generate shear waves towards the tissue within the region of interest, wherein the elastic image of the tissue quantifies a response of the tissue to the shear waves. In a second example of the method optionally including the first example, controlling the scanning apparatus to generate the shear waves comprises controlling a vibrator to generate the shear waves towards the region of interest. In a third example of the method optionally including one or more of the first and second examples, the method further comprises adjusting a position of the vibrator relative to the region of interest prior to controlling the vibrator to generate the shear waves towards the region of interest. In a fourth example of the method optionally including one or more of the first through third examples, controlling the scanning apparatus to generate the shear waves comprises controlling the ultrasound transducer to generate the shear waves towards the region of interest. In a fifth example of the method optionally including one or more of the first through fourth examples, the method further comprises, during the ultrasound scan, adjusting a position of the ultrasound transducer from a first position wherein the ultrasound image is acquired to a second position, acquiring, with the ultrasound transducer at the second position, a second ultrasound image, detecting, with the artificial intelligence model, a second region of interest within the second ultrasound image including a possible tumor, and acquiring, with the ultrasound transducer, a second elastic image of tissue within the second region of interest. In a sixth example of the method optionally including one or more of the first through fifth examples, the method further comprises, during the ultrasound scan, adjusting the position of the ultrasound transducer to a third position, acquiring, with the ultrasound transducer at the third position, a third ultrasound image, detecting, with the artificial intelligence model, an absence of a possible tumor within the third ultrasound image, and responsive to detecting the absence of a possible tumor within the third ultrasound image, not acquiring an elastic image with the ultrasound transducer at the third position. In a seventh example of the method optionally including one or more of the first through sixth examples, the method further comprises displaying, with the display device, the ultrasound image, wherein the elastic image is superimposed over the ultrasound image at the region of interest.

In another embodiment, a method comprises, during an ultrasound scan of a volume of interest, controlling an ultrasound transducer to acquire a plurality of ultrasound images corresponding to two-dimensional slices across the volume of interest, evaluating, with an artificial intelligence model, each ultrasound image of the plurality of ultrasound images to detect whether a potential tumor is depicted in the plurality of ultrasound images, and responsive to detecting a region of interest including the potential tumor in an ultrasound image of the plurality of ultrasound images, controlling the ultrasound transducer to acquire an elastic image of tissue within the region of interest.

In a first example of the method, the method further comprises evaluating each ultrasound image with the artificial intelligence model upon acquisition of each ultrasound image, and controlling the ultrasound transducer to acquire the elastic image of the tissue within the region of interest after acquiring the ultrasound image and prior to acquiring other ultrasound images of the plurality of ultrasound images. In a second example of the method optionally including the first example, controlling the ultrasound transducer to acquire the elastic image of the tissue within the region of interest comprises controlling the ultrasound transducer to image deformation of the tissue responsive to shear waves. In a third example of the method optionally including one or more of the first and second examples, the method further comprises controlling a vibrator to generate the shear waves towards the tissue within the region of interest, wherein the elastic image of the tissue quantifies the deformation of the tissue responsive to the shear waves, the vibrator mounted to a frame wherein the ultrasound transducer translates across an opening defined by the frame during the ultrasound scan. In a fourth example of the method optionally including one or more of the first through third examples, the method further comprises displaying the ultrasound image with the elastic image superimposed over the ultrasound image at the region of interest.

In yet another embodiment, a system comprises an ultrasound transducer, a display device, and a computing device communicatively coupled to the ultrasound transducer and the display device, the computing device configured with instructions in non-transitory memory that when executed cause the computing device to: acquire, with the ultrasound transducer during an ultrasound scan, an ultrasound image; detect, with an artificial intelligence model stored in the non-transitory memory, a region of interest within the ultrasound image including a possible tumor; acquire, with the ultrasound transducer, an elastic image of tissue within the region of interest; and display, with the display device, the elastic image.

In a first example of the system, the system further comprises a housing wherein the ultrasound transducer is mounted within a frame of the housing, and a motor configured to adjust a position of the ultrasound transducer relative to the frame of the housing, wherein the computing device is further configured with executable instructions in the non-transitory memory that when executed cause the computing device to, during the ultrasound scan: control the motor to adjust a position of the ultrasound transducer from a first position wherein the ultrasound image is acquired to a second position; acquire, with the ultrasound transducer at the second position, a second ultrasound image; detect, with the artificial intelligence model, a second region of interest within the second ultrasound image including a possible tumor; acquire, with the ultrasound transducer, a second elastic image of tissue within the second region of interest; and display, with the display device, the second elastic image. In a second example of the system optionally including the first example, the system further comprises a vibrator mounted to the frame of the housing, wherein the computing device is further configured with executable instructions in the non-transitory memory that when executed cause the computing device to: control the vibrator to generate shear waves towards the tissue within the region of interest while the ultrasound transducer acquires the elastic image, and control the vibrator to generate shear waves towards the tissue within the second region of interest while the ultrasound transducer acquires the second elastic image. In a third example of the system optionally including one or more of the first and second examples, the computing device is further configured with executable instructions in the non-transitory memory that when executed cause the computing device to: control a motor to adjust a position of the vibrator relative to the region of interest prior to controlling the vibrator to generate the shear waves towards the tissue within the region of interest. In a fourth example of the system optionally including one or more of the first through third examples, the computing device is further configured with executable instructions in the non-transitory memory that when executed cause the computing device to: control the ultrasound transducer to generate shear waves towards the tissue within the region of interest prior to acquiring the elastic image, and control the ultrasound transducer to generate shear waves towards the tissue within the second region of interest prior to acquiring the second elastic image, wherein the elastic image and the second elastic image depict response of the tissue within the region of interest and the tissue within the second region of interest respectively to the shear waves. In a fifth example of the system optionally including one or more of the first through fourth examples, the computing device is further configured with executable instructions in the non-transitory memory that when executed cause the computing device to: adjust the position of the ultrasound transducer to a third position; acquire, with the ultrasound transducer at the third position, a third ultrasound image; detect, with the artificial intelligence model, an absence of a possible tumor within the third ultrasound image; and responsive to detecting the absence of a possible tumor within the third ultrasound image, not acquire an elastic image with the ultrasound transducer at the third position. In a sixth example of the system optionally including one or more of the first through fifth examples, the computing device is further configured with executable instructions in the non-transitory memory that when executed cause the computing device to: control the ultrasound transducer with an acoustic beam sequence for shear wave detection to acquire the elastic image, wherein the acoustic beam sequence for shear wave detection is different from an acoustic beam sequence for acquiring the ultrasound image.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
acquiring, with an ultrasound transducer of a scanning apparatus during an ultrasound scan of a patient, a plurality of ultrasound images at a plurality of positions relative to a volume, the plurality of ultrasound images including a first image and a second image;
detecting, with an artificial intelligence model, a first region of interest within the first image and a second region of interest within the second image that include a possible tumor, wherein the first region of interest is at a first position relative to the first image, wherein the first position relative to the first image is different than a second position relative to the second image for the second region of interest, wherein the first region of interest and the second region of interest are different sizes, and wherein the first region of interest and the second region of interest correspond to different image slices within the volume;
acquiring, with a vibrator of the scanning apparatus and the ultrasound transducer, an elastic image of tissue within each region of interest, including a first elastic image for the first region of interest and a second elastic image for the second region of interest, wherein the vibrator is controlled based on a size and a position of the region of interest to generate shear waves towards the region of interest that are used to acquire the elastic image; and
displaying, with a display device, the elastic images.

2. The method of claim 1, wherein the elastic images of the tissue quantify a response of the tissue to the shear waves.

3. The method of claim 1, wherein an amplitude of the shear waves is increased or decreased based on the size and the position of the region of interest.

4. The method of claim 1, further comprising adjusting a position of the vibrator relative to the region of interest prior to controlling the vibrator to generate the shear waves towards the region of interest.

5. The method of claim 1, wherein a shape of the shear waves is adjusted based on the size and the position of the region of interest.

6. The method of claim 1, further comprising, during the ultrasound scan:
adjusting the position of the ultrasound transducer to a third position;
acquiring, with the ultrasound transducer at the third position, a third ultrasound image;
detecting, with the artificial intelligence model, an absence of a possible tumor within the third ultrasound image; and
responsive to detecting the absence of a possible tumor within the third ultrasound image, not acquiring an elastic image with the ultrasound transducer at the third position.

7. The method of claim 1, further comprising detecting a first object in the first region of interest that is likely the tumor and detecting a second object in the second region of interest that is likely the tumor, wherein a position of the first object relative to the first image is different than a position of the second object relative to the second position.

8. The method of claim 1, wherein determining the first region of interest and includes the artificial intelligence model detecting lesions or tumors within the first image, and wherein, responsive to detecting the lesions of tumors, the artificial intelligence model outputs the first position for the first region of interest and a first size for the first region of interest that includes the lesion or tumor detected within the first image.

9. The method of claim 1, wherein a third image of the plurality of ultrasound images is acquired, and wherein the third image is detected as being a null region of interest where an absence of a possible tumor is detected.

10. A method, comprising:
during an ultrasound scan of a volume of interest, controlling an ultrasound transducer of a scanning apparatus to acquire a plurality of ultrasound images corresponding to two-dimensional slices, wherein the plurality of ultrasound images includes a first image and a second image at different positions across the volume of interest;
evaluating, with an artificial intelligence model, each ultrasound image of the plurality of ultrasound images, including the first image and the second image, to detect whether a potential tumor is depicted in the plurality of ultrasound images; and
responsive to detecting a first region of interest including the potential tumor within the first image and a second region of interest including the potential tumor within the second image of the plurality of ultrasound images, controlling the ultrasound transducer and a vibrator of the scanning apparatus to acquire an elastic image of tissue within each region of interest, including a first elastic image for the first region of interest and a second elastic image for the second region of interest,
wherein the first region of interest is at a first position relative to the first image,
wherein the first position relative to the first image is different than a second position relative to the second image for the second region of interest,
wherein the first region of interest and the second region of interest are different sizes,
wherein the first region of interest and the second region of interest correspond to different image slices within the volume of interest, and
wherein the vibrator is controlled based on a size and a position of the region of interest to generate shear waves towards the region of interest that are used to acquire the elastic image.

11. The method of claim 10, further comprising evaluating each ultrasound image with the artificial intelligence model upon acquisition of each ultrasound image, and controlling the ultrasound transducer to acquire the elastic image of the tissue within the first region of interest after acquiring the first image and prior to acquiring other ultrasound images of the plurality of ultrasound images.

12. The method of claim 10, wherein controlling the ultrasound transducer to acquire the elastic image of the tissue within the region of interest comprises controlling the ultrasound transducer to image deformation of the tissue responsive to the shear waves.

13. The method of claim 12, wherein the elastic image of the tissue quantifies the deformation of the tissue responsive to the shear waves, the vibrator mounted to a frame wherein the ultrasound transducer translates across an opening defined by the frame during the ultrasound scan.

14. The method of claim 10, wherein a shape of the shear waves is adjusted based on the size and the position of the region of interest.

15. A system, comprising:
- an ultrasound transducer;
- a display device;
- a vibrator; and
- a computing device communicatively coupled to the ultrasound transducer and the display device, the computing device configured with instructions in non-transitory memory that when executed cause the computing device to:
  - acquire, with the ultrasound transducer during an ultrasound scan, a plurality of ultrasound images at different positions relative to a volume, the plurality of ultrasound images including a first image and a second image;
  - detect, with an artificial intelligence model stored in the non-transitory memory, a first region of interest within the first image and a second region of interest within the second image including a possible tumor, wherein the first region of interest is at a first position relative to the first image, wherein the first position relative to the first image is different than a second position relative to the second image for the second region of interest, wherein the first region of interest and the second region of interest are different sizes, and wherein the first region of interest and the second region of interest correspond to different image slices within the volume;
  - acquire, with the vibrator and the ultrasound transducer, an elastic image of tissue within each region of interest, including a first elastic image of the first region of interest and a second elastic image of the second region of interest, wherein the vibrator is controlled based on a size and a position of the region of interest to generate shear waves towards the region of interest that are used to acquire the elastic image; and
  - display, with the display device, the elastic images.

16. The system of claim 15, further comprising a housing wherein the ultrasound transducer is mounted within a frame of the housing, and a motor configured to adjust a position of the ultrasound transducer relative to the frame of the housing, wherein the computing device is further configured with executable instructions in the non-transitory memory that when executed cause the computing device to, during the ultrasound scan:
- control the motor to adjust the position of the ultrasound transducer from a first position wherein the first image is acquired to a second position; and
- acquire, with the ultrasound transducer at the second position, the second image.

17. The system of claim 16, wherein the vibrator is mounted to the frame of the housing, wherein the computing device is further configured with executable instructions in the non-transitory memory that when executed cause the computing device to: control the vibrator to generate the shear waves towards the tissue within the region of interest while the ultrasound transducer acquires the elastic image.

18. The system of claim 17, wherein the computing device is further configured with executable instructions in the non-transitory memory that when executed cause the computing device to: control a motor to adjust a position of the vibrator relative to the region of interest prior to controlling the vibrator to generate the shear waves towards the tissue within the region of interest.

19. The system of claim 16, wherein a shape of the shear waves is adjusted based on the size and the position of the region of interest, and wherein an amplitude of the shear waves is increased or decreased based on the size and position of the region of interest to acquire the elastic image.

20. The system of claim 16, wherein the computing device is further configured with executable instructions in the non-transitory memory that when executed cause the computing device to:
- adjust the position of the ultrasound transducer to a third position;
- acquire, with the ultrasound transducer at the third position, a third ultrasound image;
- detect, with the artificial intelligence model, an absence of a possible tumor within the third ultrasound image; and
- responsive to detecting the absence of a possible tumor within the third ultrasound image, not acquire an elastic image with the ultrasound transducer at the third position.

* * * * *